United States Patent [19]

Greenwald

[11] 3,958,992

[45] May 25, 1976

[54] 1,3-DISULFONYLCYCLOALKANES AS SILVER HALIDE SOLVENTS

[75] Inventor: Richard B. Greenwald, Lexington, Mass.

[73] Assignee: Polaroid Corporation, Cambridge, Mass.

[22] Filed: Dec. 23, 1974

[21] Appl. No.: 535,205

[52] U.S. Cl. ................................ 96/29 R; 96/61 R; 96/61 M
[51] Int. Cl.² .................. G03C 5/54; G03C 5/38
[58] Field of Search ............ 96/61 R, 60 BF, 61 M, 96/29 R; 260/327 M

[56] References Cited
UNITED STATES PATENTS 2,767,195   10/1956   Brockman et al. ............ 260/327 M
3,769,014   10/1973   Stewart et al. ..................... 96/61 R

OTHER PUBLICATIONS

"Stereochemistry of α–Sulfonyl Carbanions," Corey et al., *Tetrahedron Letters*, No. 12, pp. 515–520, 1962.

*Primary Examiner*—Mary F. Kelley
*Assistant Examiner*—Richard L. Schilling
*Attorney, Agent, or Firm*—Sybil A. Campbell

[57] ABSTRACT

1,3-disulfonylcycloalkanes substituted in the 2-position with at least one hydrogen atom are employed as silver halide complexing agents in both conventional and diffusion transfer photography. Preferred compounds are those possessing an S-containing moiety substituted in the 2-position and particularly those containing 6, 7 or 8 members in the cyclic ring and substituted in the 2-position with $R^2-S(CH_2)_m$ wherein $R^2$ is a hydrocarbon radical and m is a whole number 0 to 5. The latter thioether-substituted 1,3-disulfonylcycloalkanes comprise the novel compounds of the present invention.

23 Claims, No Drawings

1,3-DISULFONYLCYCLOALKANES AS SILVER HALIDE SOLVENTS

BACKGROUND OF THE INVENTION

1. Field of the Invention

This invention relates to photography and, in particular, it is concerned with a new class of silver halide solvents and with photographic products, processes and compositions employing the same.

2. Description of the Prior Art

Photographic processing compositions capable of forming water-soluble complex silver salts are known to be useful in many types of silver halide photography. To obtain a relatively stable image in an exposed and developed photosensitive silver halide emulsion, the silver halide remaining in the unexposed and undeveloped areas of the emulsion should be converted to a soluble silver complex that can be removed by washing or converted to a stable silver complex that will not "print-out" upon prolonged exposure to light. In conventional or "tray" development, it is customary to fix the developed silver halide emulsion by applying a solution of silver halide solvent, i.e., silver halide complexing agent which forms a water-soluble silver complex with the residual silver halide. The water-soluble silver complex thus formed and excess silver halide solvent are then removed from the developed and fixed emulsion by washing with water.

Silver halide solvents also have been employed in monobaths where a single processing composition containing a silver halide developing agent in addition to the silver halide solvent is utilized for both developing and fixing an exposed photosensitive silver halide layer. Silver halide solvents also have been employed in diffusion transfer photographic processes. Such processes are now well known in the art; see for example, U.S. Pat. Nos. 2,543,181; 2,647,056; 2,983,606; etc. In processes of this type, an exposed silver halide emulsion is treated with a processing composition whereby the exposed silver halide emulsion is developed and an imagewise distribution of diffusible image-forming components is formed in the unexposed and undeveloped portions of the silver halide emulsion. This distribution of image-forming components is transferred by imbibition to an image-receiving stratum in superposed relationship with the silver halide emulsion to provide the desired transfer image. In diffusion transfer processes where a silver transfer image is formed, processing is effected in the presence of a silver halide solvent which forms a diffusible complex with the undeveloped silver halide. The soluble silver complex thus formed diffuses to the superposed image-receiving layer where the transferred silver ions are deposited as metallic silver to provide the silver transfer image. In preparing silver prints in this manner the image-receiving element preferably includes a silver precipitating agent, for example, heavy metal sulfides and selenides as described in U.S. Pat. No. 2,698,237 of Edwin H. Land.

Various compounds have beem employed as silver halide solvents in the photographic processes described above. One of the most commonly employed is sodium thiosulfate. Other silver halide solvents that have been used include thiocyanates, such as potassium and sodium thiocyanate; mercaptans, such as mercaptoacetic acid and cysteine; alkali metal cyanides, such as potassium cyanide; and cyclic imides, such as barbituric acid and uracil. U.S. Pat. No. 3,769,014 discloses still another class of silver halide solvents, namely, β-disulfones but is limited to the use of open-chain compounds, i.e., 1,1-bis-sulfonyl alkanes though various cyclic β-disulfones are known per se in the art.

According to the present invention, it has been found that certain cyclic β-disulfones are also useful as silver halide solvents.

SUMMARY OF THE INVENTION

It is, therefore, the primary object of the present invention to provide photographic products, processes and compositions employing certain cyclic β-disulfones silver halide solvents.

It is another object of this invention to provide novel β-disulfones useful as photographic silver halide solvents.

Other objects of this invention will in part be obvious and will in part appear hereinafter.

The invention accordingly comprises the processes involving the several steps and the relation and order of one or more of such steps with respect to each of the others, and the products and compositions possessing the features, properties and the relation of elements which are exemplified in the following detailed disclosure, and the scope of the application of which will be indicated in the claims.

For a fuller understanding of the nature and objects of the invention, reference should be had to the following detailed description.

DETAILED DESCRIPTION OF THE INVENTION

As noted above, it has now been found that cyclic β-disulfones are useful for complexing silver ion, i.e., undeveloped silver halide in photographic processes. Cyclic β-disulfones found particularly useful in both conventional and diffusion transfer photography are 1,3-disulfonylcycloalkanes, i.e., cyclic alkanes with two intralinear $-SO_2-$ groups positioned β to each other, which possess 6, 7 or 8 members in the cyclic ring (including said sulfonyl groups) and wherein the 2-carbon atom is substituted with at least one hydrogen atom. Particularly useful compounds of this type are those represented in the following formula:

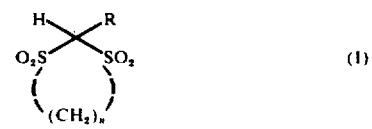

(I)

werein R is hydrogen or a monovalent organic radical and n is a whole number 3, 4 or 5.

As used herein, "monovalent organic radical" is intended to include both cyclic and acyclic organic radicals whether homogeneous or heterogeneous in nature. Typical radicals useful as the R moiety are alkyl, substituted and unsubstituted; alkyl wherein the carbon chain is interrupted with a heteroatom, substituted and unsubstituted; cycloalkyl, substituted and unsubstituted; alkenyl, substituted and unsubstituted; cycloalkenyl, substituted and unsubstituted; and aryl, substituted and unsubstituted. Generally, the substituents of the substituted monovalent organic radicals are solubilizing groups, i.e., groups selected to make the compound soluble in the particular liquid vehicle used. Typical of such substituents are $-SO_3H$, $-OH$, $-NH_2$ and $-COOH$, particularly where the liquid vehicle is aqueous. Among other substituents that may be present, if desired, are halo, nitro, cyano, and alkoxy.

In the above-described 1,3-disulfonylcycloalkanes, the proton (hydrogen) on the carbon atom in the 2-position is removable in alkali to provide the corresponding C⁻ anion. In a preferred embodiment, the R substituent is a moiety containing —S—, excluding —SH and moieties that would form —SH in alkali, wherein said sulfur atom of said moiety is positioned adjacent to or up to 6 or 7 atoms away from said carbon atom. The —S— containing moiety preferably is R′λS—(X)$_m$— wherein R′ is a monovalent organic radical, usually a hydrocarbon radical, which may be unsubstituted or substituted with e.g., a solubilizing group or groups; X represents a carbon atom, a heteroatom or a mixture of carbon atoms and heteroatoms and m is a whole number 0 to 5. The —S— of said R′S—(X)$_m$— moiety should be in a positon alpha, beta, gamma, delta, epsilon or zeta to the C⁻ anion as illustrated below wherein Y represents the residue of the 1,3-disulfonylcycloalkane:

| | |
|---|---|
| Y—C⁻—SR′ | alpha |
| Y—C⁻—X—SR′ | beta |
| Y—C⁻—X—X—SR′ | gamma |
| Y—C⁻—X—X—X—SR′ | delta |
| Y—C⁻—X—X—X—X—SR′ | epsilon |
| Y—C⁻—X—X—X—X—X—SR′ | zeta |

Preferably, the position of —S— with respect to the C⁻ anion is alpha, gamma, delta, epsilon or zeta.

The compounds substituted with an —S— containing moiety as described above comprise per se novel compound within the present invention. In a particularly preferred embodiment, the subject compounds have the formula:

(II)

wherein R¹ is R²—S—(CH₂)$_m$ wherein R² is a hydrocarbon radical containing up to about 20 carbon atoms selected from alkyl, aryl, alkaryl and aralkyl, said hydrocarbon radical being unsubstituted or substituted with a solubilizing group selected from carboxy, sulfo, hydroxy and amino, m is a whole number 0, 1, 2, 3, 4 or 5 and n is a whole number 3, 4 or 5. Preferably, R² is lower alkyl containing 1 to 4 carbon atoms, unsubstituted or substituted with a solubilizing group and n is 3 or 4.

Illustrative R² groups include alkyl, such as, methyl, ethyl, propyl, isopropyl, n-butyl, t-butyl, hexyl, octyl, dodecyl, hexadecyl and octadecyl; aryl, such as phenyl and naphthyl; alkaryl, such as p-hexylphenyl, p-octylphenyl and p-dodecylphenyl; and aralkyl, such as benzyl, phenethyl and phenylhexyl. As mentioned above, to enhance the solubility of the compound in aqueous alkaline solution, the R² group may be substituted with a solubilizing group(s), such as those enumerated above. Preferred substituted R² $^{groups\ are\ \omega\text{-}R3}$-alkyl, w-R³-alkaryl, p-R³-aryl and p-R³-aralkyl wherein R³ is carboxy, hydroxy, sulfo or amino, i.e., —NR₁R₂ wherein R₁ and R₂ each are selected from hydrogen and alkyl, preferably lower alkyl containing 1 to 4 carbon atoms.

Specific examples of compounds useful as silver halide solvents in accordance with the present invention are those set out in the following formulas. It will be appreciated that those compounds substituted with an —S— containing moiety as described above illustrate the per se novel compounds of the present invention.

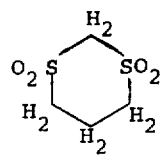

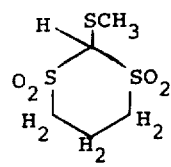

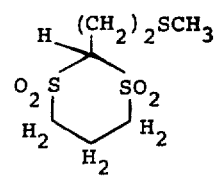

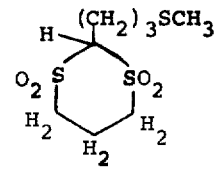

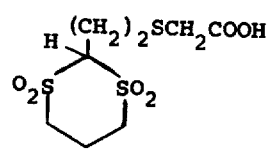
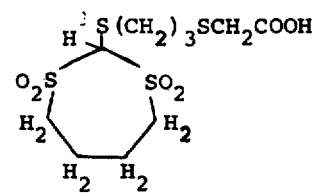
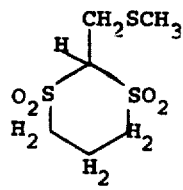
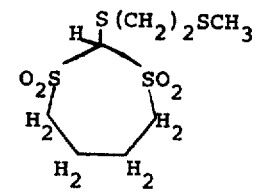
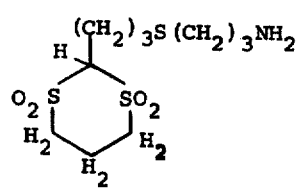
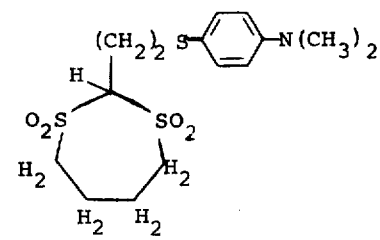
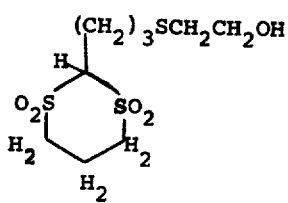
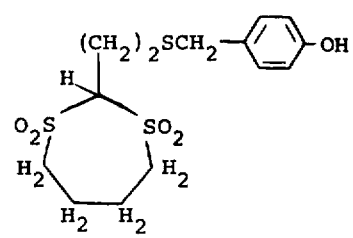
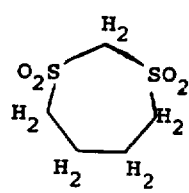
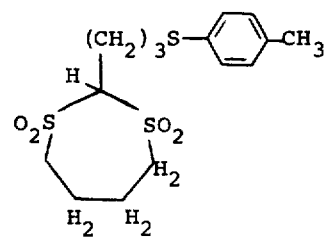
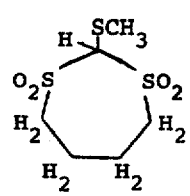
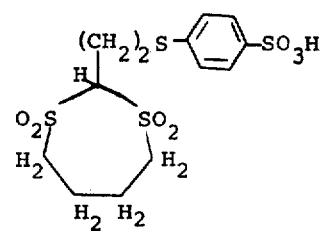

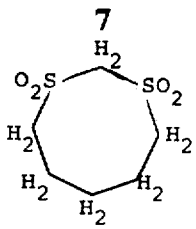

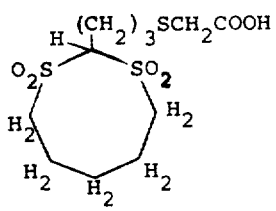

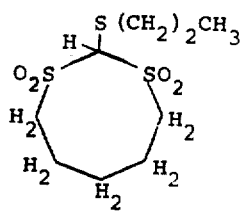

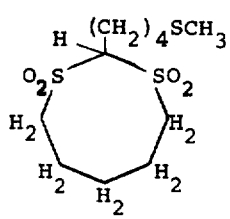

The non-S-substituted 1,3-disulfonylcycloalkanes may be synthesized in a conventional manner from the corresponding 1,3-dithiocycloalkanes, such as, 1,3-dithiane and 1,3-dithiepane as described, for example, in Ber., 32, p. 1375 (1899) and Tetrahedron Letters, 1962, p. 515. The compounds substituted with the —S— containing moiety may be prepared, for example, by reacting the 1,3-disulfonylcycloalkane with the chlorosubstituted derivative of the selected $R^1$ substituent, i.e., $R^2$—S—$(CH_2)_m$—Cl as described in the following examples which are intended to be illustrative only.

EXAMPLE I

Preparation of the compound of formula (2):

In a 3-neck round bottom flask fitted with thermometer, dropping funnel and air condenser, 1,3-dithiane (20 g., 0.166 mole) was dissolved in 100 ml. glacial acetic acid. A solution of commercial 40% peracetic acid (139 g., about 0.73 mole) was diluted with 100 ml. glacial acetic acid and was added dropwise over 1 hour and the temperature maintained at about 70° C. A large amount of white solid crystallized from the reaction mixture. After heating for an additional one hour at 60°–70° C., the solid was collected, pressed dry, slurried with water, collected, and pressed dry. Final drying was effected by washing with a small volume of cold methanol followed by ether to give 28.7 g. (94% by weight) of 1,3-dithiane disulfone (1,3-dithiane-1,1,3,3-tetraoxide), the compound of formula 1.

In a dry 3-neck round bottom flask fitted with a dropping funnel, thermometer, air condenser with nitrogen inlet and magnetic stirrer, 1,3-dithiane disulfone (6.7 g., 36.4 mmoles) was suspended in 80 ml. of N,N-dimethylformamide. Sodium hydride (57% mineral oil dispersion, 1.53 g., 36.4 mmoles) was added in portions. The reaction mixture was stirred at 40° C. for 1 hour to give a gray solution. A solution of methylthiotosylate (7.36 g., 36.4 mmoles) in 10 ml. dimethylformamide was added dropwise. A voluminous precipitate formed. The reaction mixture was heated to 80° C. and maintained for 3 hours to obtain a nearly homogeneous reaction mixture. The resulting homogeneous mixture was allowed to cool and then poured onto ice containing 4 ml. concentrated hydrochloric acid. The off-white solid was collected and air-dried (approximately 8 g., melting range 271°–5° C.). The crude product was recrystallized from hot N,N-dimethylformamide (1 g./3 ml.) and clarified with Norit to give 2.6 g. (31% by weight) of the title compound, melting range 280°–282° C. A second crop of the title compound (2.3 g., 28% by weight) was obtained by diluting wih an equal volume of water.

|  | C | H |
|---|---|---|
| Theory | 26.05 | 4.35 |
| Found | 26.4 | 4.40 |

EXAMPLE II

Preparation of the compound of formula (3):

A warm slurry of 1,3-dithiane disulfone (18.4 g., 100 mmoles) in approximately 200 mls. of N,N-dimethylformamide was added to a slurry of sodium hydride (57% mineral oil dispersion, 42 g., 100 mmoles) in approximately 30 mls. of N,N-dimethylformamide.

This mixture was stirred for about one-half hour at 50°–60° C. to give a clear gray solution. 2-chloroethylmethylsulfide was added dropwise to the solution over 15 minutes and stirring was continued at 50°–60° C. overnight. The resulting yellow-brown solution (some white granular solid separated) was poured into 1 liter of ice water containing 10 mls. of concentrated hydrochloric acid to give a gray solid. The gray solid was triturated with ether, and 5 g. of the crude product was recrystallized from 125 mls. of hot ethanol to give 2.3 g. of the title compound as a white solid (melting point 157° C.).

|  | C | H | S |
|---|---|---|---|
| Theory | 32.6 | 5.43 | 37.2 |
| Found | 32.6 | 5.38 | 37.45 |

EXAMPLE III

Preparation of the compound of formula (4):

1,3-dithiane disulfone (2.5 g., 13.6 mmoles) and sodium hydride (57% mineral oil dispersion, 0.57 g., 13.6 mmoles) were stirred together in 30 mls. of N,N-dimethylformamide for about 2 hours at a temperature of about 35° C. under nitrogen. 3-chloropropylmethylsulfide (1.7 g., 13.6 mmoles) was added, and the reaction mixture was stirred at about 65° C. overnight. The formation of solid was noticeable after about one-half hour. The reaction mixture was poured onto ice concentrated hydrochloric acid (3ml.). The white solid was collected and triturated with petroleum ether. Recrystallization from 100 mls. of hot ethanol gave 2 g. of the title compound as a white solid (melting range 133°–136° C.).

EXAMPLE IV

Preparation of the compound of formula (5):

Sodium hydride (57% mineral oil dispersion, 1.35 g., 32.8 mmoles) was added in one portion to a suspension of 1,3-dithiane disulfone in 35 mls. of N,N-dimethylformamide, and the mixture was stirred about 45 minutes at 40°–50° C. to give a gray solution. S-(2-chloroethyl)-ethylmercaptoacetate (6 g., 32.8 mmoles) in 15 mls. of N,N-dimethylformamide was added dropwise to the solution over 15 minutes with stirring and stirring was continued at room temperature overnight. The reaction mixture was then poured onto ice concentrated acid (3 ml.). A taffy separated which soon solidified on scratching. This solid was collected, washed well with water and triturated with petroleum ether. Of the 7.3 g. of solid collected, approximately 5 g. was recrystallized from 100 mls. of methanol. About 0.9 g. of insolubles was discarded, and about 2.0 g. of the ester intermediate was recovered as white needles (melting range 126°–128° C.).

Hydrochloric acid (4 mls. of approximately 3N acid) was added to a suspension of the ester prepared above in 10 mls. ethanol. The mixture was heated to reflux, and a solution was obtained in about 10 minutes. Heating was continued for about 3 hours. The solution was then allowed to cool and stand overnight. The white crystalline material that formed was collected and discarded, and 4 mls. of approximately 5N hydrochloric acid was added to the solution. After heating at reflux for 6 hours, 10 mls. of water was added and heating at reflux was continued overnight. The solution was cooled and the ethanol stripped leaving a white crystalline solid. 10 mls. of 6N hydrochloric acid was added to the crystalline material. The resulting solution was heated at reflux for about 4 hours and then stripped to give a solid which was triturated with ether and collected (about 1.0 g.). The solid was taken up in about 13 mls. of hot water, the solution quickly cooled to room temperature, filtered and allowed to stand at room temperature for 2 days. The title compound was then recovered as white clusters (melting range 151°–152° C.).

EXAMPLE V

Preparation of the compound of formula (9):

A sample of partially purified 1,3-dithiepane [prepared according to Tetrahedron, 20, 427 (1964)](1.5 g., about 10 mmoles) was dissolved in glacial acetic acid, and 40% peracetic acid (10 g., about 50 mmoles) was added slowly dropwise. The reaction was allowed to stir overnight at room temperature when the white solid precipitate was collected and washed with water to give approximately 50% crude product (melting range 175°–178°C.) which was homogeneous by TLC. Recrystallization from hot water afforded the title compound, 1,3-dithiepane-1,1,3,3-tetraoxide, as white needles (melting range 190°–192°C.)

In formulating photographic processing compositions utilizing the above-described compounds, the compounds may be used singly or in admixture with each other. The total amount employed may vary widely depending upon the particular photographic system and should be used, for example, in a quantity sufficient for fixing a developed negative in conventional tray processing or in a quantity sufficient to give a satisfactory transfer print in diffusion transfer processes under the particular processing conditions employed.

Though the silver halide solvents of the present invention are broadly useful in a variety of photographic processes of the type in which water-soluble silver complexes are formed from the unreduced silver halide of a photoexposed and at least partially developed silver halide stratum, they find particular utility in diffusion transfer processes. A composition embodying the present invention specifically suitable for use in the production of transfer images comprises, in addition to the silver halide complexing agents of the above-described type, a suitable silver halide developing agent, preferably an organic developing agent. Examples of developing agents that may be employed include hydroquinone and substituted hydroquinones, such as tertiary butyl hydroquinone, 2,5-dimethyl hydroquinone, methoxyhydroquinone, ethoxyhydroquinone, chlorohydroquinone; pyrogallol and catechols, such as catechol, 4-phenyl catechol and tertiary butyl catechol; aminophenols, such as 2,4,6-diamino-orthocresol; 1,4-diaminobenzenes, such as p-phenylenediamine, 1,2,4-triaminobenzene and 4-amino-2-methyl-N,N-diethylaniline; ascorbic acid and its derivatives, such as ascorbic acid, isoascorbic acid and 5,6-isopropylidene ascorbic acid and other enediols, such as tetramethyl reductic acid; and hydroxylamines, such as N,N-di-(2-ethoxyethyl)hydroxylamine and N,N-di-(2-methoxyethyl)hydroxylamine.

In diffusion transfer processes, the processing composition, if it is to be applied to the emulsion by being spread thereon in a thin layer, also usually includes a viscosity-imparting reagent. The processing composition may comprise, for example, one or more silver halide solvents of the present invention, one or more conventional developing agents such as those enumerated above, an alkali such as sodium hydroxide or potassium hydroxide and a viscosity-imparting reagent such as a high molecular weight polymer, e.g., sodium carboxymethyl cellulose or hydroxyethyl cellulose.

In one such transfer process, the processing solution is applied in a uniformly thin layer between the superposed surfaces of a photoexposed photosensitive element and an image-receiving element, for example, by advancing the elements between a pair of pressure-applying rollers. The elements are maintained in superposed relation for a predetermined period, preferably for a duration of 15 to 120 seconds, during which exposed silver halide is reduced to silver and unreduced silver halide forms a water-soluble, complex salt which diffuses through the layer of solution to the image-receiving element, there to be reduced to an argental image. At the end of this period, the silver halide element is separated from the image receiving element. Materials useful in such a transfer process are described in U.S. Pat. No. 2,543,181, issued in the name of Edwin H. Land on Feb. 27, 1951, and in numerous other patents.

The photosensitive element may be any of those conventionally used in silver diffusion transfer processes and generally comprises a silver halide emulsion carried on a base, e.g., glass, paper or plastic film. The silver halide may be a silver chloride, iodide, bromide, iodobromide, chlorobromide, etc. The binder for the halide, though usually gelatin, may be a suitable polymer such as polyvinyl alcohol, polyvinyl pyrrolidone and their copolymers.

The image-receiving element preferably includes certain materials, the presence of which, during the transfer process has a desirable effect on the amount and character of silver precipitated on the image-receiving element. Materials of this type are specifically described in U.S. Pat. Nos. 2,690,237 and 2,698,245, both issued in the name of Edwin H. Land on Dec. 28, 1954.

Separating of the silver halide element from the image-receiving element may be controlled so that the layer of processing composition is removed from the image-receiving element or the layer of processing composition is caused to remain in contact with the image-receiving element, e.g., to provide it with a protective coating. Techniques which enable such results to be accomplished as desired are described in U.S. Pat. No. 2,647,054 issued to Edwin H. Land on July 28, 1953. In general, the processing reagents are selected so that traces remaining after the solidified processing layer has been separated from the silver image or which remain in said layer adhered as a protective coating on the silver image, as indicated above, are colorless or pale, so as not to appreciably affect the appearance of the image and to have little or no tendency to adversely react with the silver image.

The silver halide solvents of the present invention also may be employed in diffusion transfer processes adapted to provide positive silver transfer images which may be viewed as positive transparencies without being separated from the developed negative silver image including such processes adapted for use in forming additive color projection positive images. Diffusion transfer processes of this type are described in U.S. Pat. Nos. 3,536,488 of Edwin H. Land and 3,615,428 of Lucretia J. Weed and U.S. application Ser. No. 383,196 of Edwin H. Land filed July 27, 1973. The subject compounds also find utility as silver halide solvents in diffusion transfer processes utilizing the properties of the imagewise distribution of silver ions in the soluble silver complex made available in the undeveloped and partially developed areas of a silver halide emulsion to liberate a reagent, e.g., a dye in an imagewise fashion, as described in U.S. Pat. No. 3,719,489 of Ronald F. W. Cieciuch, Roberta R. Luhowy, Frank A. Meneghini and Howard G. Rogers.

The following example is given to illustrate the utility of the compounds of the present invention as photographic silver halide solvents and is not intended to be limiting.

EXAMPLE VI

A negative comprising a photosensitive silver halide emulsion was exposed to a step wedge and processed by spreading a layer of processing composition approximately 1.2 mils. thick between the exposed emulsion and a superposed image-receiving element comprising a layer of regenerated cellulose containing colloidal palladium sulfide carried on a transparent support. The processing composition was prepared by adding a silver solvent of the present invention in a concentration of 5% by weight to the following formulation:

| | |
|---|---|
| Water | 814.0 g. |
| Potassium hydroxide (Aqueous 50% w/w solution) | 348.0 g. |
| Hydroxyethyl cellulose | 35.0 g. |
| Zinc acetate | 15.0 g. |
| Triethanolamine | 5.6 g. |
| Bis-N,N-methoxyethyl hydroxylamine | 50.0 g. |

After an imbibition period of approximately one minute, the negative was separated from the image-receiving element, and the maximum and minimum transmission densities were measured for the positive image.

The compounds added to the base formulation as silver halide solvents, and the density measurements for the positive image obtained with each of the compounds are set forth in the following table:

TABLE

| Compound (Formula No.) | Density | |
|---|---|---|
| | Maximum | Minimum |
| (1) | 1.60 | 0.40 |
| (2) | 0.95 | 0.08 |
| (5) | 1.20 | 0.10 |
| (9) | 2.60 | 0.80 |

In a visual comparison of the negative images obtained with the compounds listed in the above table, it was observed that the compounds substituted with the —S— containing moiety enhanced negative fixing, i.e., lower background. Also, it was observed that a substantial increase in positive speed, approximately 4 to 5 stops, was obtained with these substituted compounds.

It will be apparent that the relative proportions of the subject silver halide solvents and of the other ingredients of the processing compositions may be varied to suit the requirements of a given photographic system. Also, it is within the scope of this invention to modify the formulations set forth above by the substitution of alkalies, antifoggants and so forth other than those specifically mentioned. Where desirable, it is also contemplated to include in the processing compositions, other components as commonly used in the photographic art.

Since certain changes may be made in the above compositions and processes without departing from the scope of the invention herein involved, it is intended that all matter contained in the above description should be interpreted as illustrative and not in a limiting sense.

What is claimed is:

1. A photographic processing composition comprising an aqueous alkaline processing solution of a silver halide developing agent and 1,3-disulfonylcycloalkane dissolved therein as a silver halide solvent, said 1,3-disulfonylcycloalkane possessing 6, 7, or 8 members in in the cyclic ring and substituted in the 2-position with at least one hydrogen atom.

2. A photographic processing composition as defined in claim 1 wherein said 1,3-disulfonylcycloalkane is substituted in the 2-position with two hydrogen atoms.

3. A photographic processing composition as defined in claim 2 wherein said 1,3-disulfonylcycloalkane is 1,3-dithione-1,1,3,3-tetraoxide.

4. A photographic processing composition as defined in claim 2 wherein said 1,3-disulfonylcycloalkane is 1,3-dithiepane-1,1,3,3-tetraoxide.

5. A photographic processing composition as defined in claim 1 wherein said 1,3-disulfonylcycloalkane is substituted in the 2-position with a hydrogen atom and a monovalent organic radical having the formula $R^2$-S-$(CH_2)_m$ wherein $R^2$ is a hydrocarbon radical containing up to 20 carbon atoms selected from alkyl, aryl, alkaryl and aralkyl, said hydrocarbon radical being unsubstituted or substituted with a solubilizing group selected from carboxy, sulfo, hydroxy and amino and m is a whole number 0, 1, 2, 3, 4 or 5.

6. A photographic processing composition as defined in claim 5 wherein said 1,3-disulfonylcycloalkane is

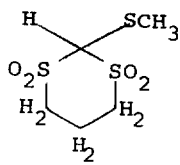

7. A photographic processing composition as defined in claim 5 wherein said 1,3-disulfonylcycloalkane is

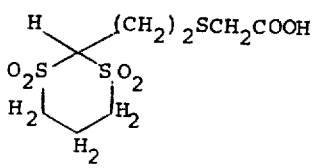

8. A photographic processing composition as defined in claim 1 which additionally includes a viscosity-increasing reagent.

9. A photographic process for forming a water-soluble complex silver salt with the unexposed and undeveloped silver halide of a photosensitive element exposed imagewise and developed but unfixed which comprises treating said silver halide with an aqueous alkaline processing composition comprising a 1,3-disulfonylcycloalkane dissolved therein as a silver halide solvent, said 1,3-disulfonylcycloalkane possessing 6, 7 or 8 members in the cyclic ring and substituted in the 2-position with at least one hydrogen atom.

10. A photographic process as defined in claim 9 wherein said 1,3-disulfonylcycloalkane is substituted in the 2-position with two hydrogen atoms.

11. A photographic process as defined in claim 10 wherein said 1,3-disulfonylcycloalkane is 1,3-dithiane-1,1,3,3-tetraoxide.

12. A photographic process as defined in claim 10 wherein said 1,3-disulfonylcycloalkane is 1,3dithiepane-1,1,3,3-tetraoxide.

13. A photographic process as defined in claim 9 wherein said 1,3-disulfonylcycloalkane is substituted in the 2-position with a hydrogen atom and a monovalent organic radical having the formula $R^2$-S-$(CH_2)_m$ wherein $R^2$ is a hydrocarbon radical containing up to 20 carbon atoms selected from alkyl, aryl, alkaryl and aralkyl, said hydrocarbon radical being unsubstituted or substituted with a solubilizing group selected from carboxy, sulfo, hydroxy and amino and m is a whole number 0, 1, 2, 3, 4 or 5.

14. A photographic process as defined in claim 13 wherein said 1,3-disulfonylcycloalkane is

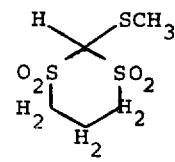

15. A photographic process as defined in claim 13 wherein said 1,3-disulfonylcycloalkane is

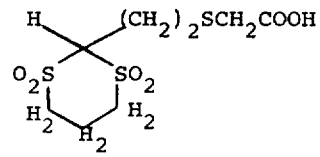

16. A diffusion transfer photographic process comprising the steps of:
1. reacting exposed silver halide of an imagewise exposed photosensitive emulsion layer carried on a support with a silver halide developing agent in aqueous alkaline solution;
2. reacting unreduced silver halide of said photosensitive emulsion with a 1,3-disulfonylcycloalkane possessing 6, 7 or 8 members in the cyclic ring and substituted in the 2-position with at least one hydrogen atom, said 1,3-disulfonylcycloalkane being capable of reacting with silver halide to form a complex silver salt that is soluble in said alkaline solution;
3. transferring said complex silver salt to a superposed image-receiving layer; and
4. reducing said transferred complex silver salt to provide a silver image.

17. A photographic process as defined in claim 16 wherein said 1,3-disulfonylcycloalkane is substituted in the 2-position with two hydrogen atoms.

18. A photographic process as defined in claim 17 wherein said 1,3-disulfonylcycloalkane is 1,3-dithiane- 1,1,3,3-tetraoxide.

19. A photographic process as defined in claim 17 wherein said 1,3-disulfonylcycloalkane is 1,3-dithiepane-1,1,3,3-tetraoxide.

20. A photographic process as defined in claim 16 wherein said 1,3-disulfonylcycloalkane is substituted in the 2-position with a hydrogen atom and a monovalent organic radical having the formula $R^2-S-(CH_2)_{\overline{m}}$ wherein $R^2$ is a hydrocarbon radical containing up to 20 carbon atoms selected from alkyl, aryl, alkaryl and aralkyl, said hydrocarbon radical being unsubstituted or substituted with a solubilizing group selected from carboxy, sulfo, hydroxy and amino and m is a whole number 0, 1, 2, 3, 4 or 5.

21. A photographic process as defined in claim 20 wherein said 1,3-disulfonylcycloalkane is

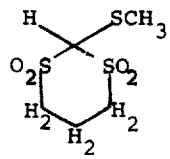

22. A photographic process as defined in claim 20 wherein said 1,3-disulfonylcycloalkane is

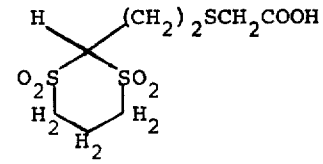

23. A photographic process as defined in claim 16 which additionally includes a viscosity-increasing reagent.

* * * * *